(12) United States Patent
Weaver et al.

(10) Patent No.: US 11,281,878 B2
(45) Date of Patent: Mar. 22, 2022

(54) WETNESS DETECTION WITH BIOMETRIC SENSOR DEVICE FOR USE IN BLOOD TREATMENT

(71) Applicant: Fresenius Medical Care Holdings, Inc., Waltham, MA (US)

(72) Inventors: Colin Weaver, Pleasanton, CA (US); Martin Joseph Crnkovich, Walnut Creek, CA (US); David Yuds, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 114 days.

(21) Appl. No.: 15/899,573

(22) Filed: Feb. 20, 2018

(65) Prior Publication Data
US 2019/0258842 A1 Aug. 22, 2019

(51) Int. Cl.
*G06K 9/00* (2006.01)
*G16H 20/17* (2018.01)
(Continued)

(52) U.S. Cl.
CPC ..... *G06K 9/00006* (2013.01); *G06K 9/00885* (2013.01); *G08B 21/20* (2013.01);
(Continued)

(58) Field of Classification Search
CPC ... G06F 1/00–2221/2153; G16H 10/00–80/00; A61B 1/00–2576/026;
(Continued)

(56) References Cited

U.S. PATENT DOCUMENTS 6,406,426 B1 6/2002 Reuss et al.
7,147,615 B2 12/2006 Wariar et al.
(Continued)

FOREIGN PATENT DOCUMENTS

EP 2939351 11/2015
EP 3010193 4/2016
(Continued)

OTHER PUBLICATIONS

Shin et al., "Designing fingerprint-recognition-based access control for electronic medical records systems," 22nd International Conference on Advanced Information Networking and Applications—Workshops, IEEE Computer Society, pp. 106-110 (Year: 2008).*

(Continued)

*Primary Examiner* — Elaine Gort
*Assistant Examiner* — Jonathon A. Szumny
(74) *Attorney, Agent, or Firm* — Fish & Richardson P.C.

(57) ABSTRACT

A device that allows for patient identification comprising a housing, a biometric sensor, coupled to the housing. the biometric sensor is configured to detect a biometric feature of a patient. The device further comprises a signal transmitter configured to transmit data related to the detected biometric feature to a medical treatment machine for carrying out a medical treatment on the patient. The patient identification device is configured to be secured to the patient during the dialysis treatment.

18 Claims, 11 Drawing Sheets

(51) Int. Cl.
*G16H 10/65* (2018.01)
*G08B 21/20* (2006.01)
*G16H 40/60* (2018.01)
*A61M 1/14* (2006.01)

(52) U.S. Cl.
CPC ............ *G16H 10/65* (2018.01); *G16H 20/17* (2018.01); *A61M 1/14* (2013.01); *A61M 2205/15* (2013.01); *G16H 40/60* (2018.01)

(58) Field of Classification Search
CPC .. A61M 1/00–2250/00; H04B 1/00–2215/069; H04W 4/00–99/00; G06K 1/00–2215/111; G08B 21/20
See application file for complete search history.

(56) References Cited

U.S. PATENT DOCUMENTS

| | | | |
|---|---|---|---|
| 7,605,710 B2 | 10/2009 | Crnkovich et al. | |
| 7,973,667 B2 | 7/2011 | Crnkovich et al. | |
| 8,981,948 B2 | 3/2015 | Olde et al. | |
| 10,561,780 B2* | 2/2020 | Childers | G16H 20/40 |
| 2001/0012917 A1 | 8/2001 | Inukai et al. | |
| 2003/0173408 A1 | 9/2003 | Mosher et al. | |
| 2010/0010427 A1* | 1/2010 | Yu | B01D 61/32 604/29 |
| 2010/0100026 A1 | 4/2010 | Morris | |
| 2010/0256473 A1* | 10/2010 | Asama | A61B 5/0002 600/365 |
| 2013/0211206 A1* | 8/2013 | Sands | A61M 1/14 600/301 |
| 2013/0317753 A1* | 11/2013 | Kamen | G06F 19/3418 702/19 |
| 2014/0012197 A1 | 1/2014 | Heppe et al. | |
| 2014/0031736 A1* | 1/2014 | Wright | A61M 1/342 604/5.01 |
| 2014/0121845 A1* | 5/2014 | Mueller | A61M 5/1413 700/282 |
| 2014/0148104 A1* | 5/2014 | Marterstock | A61M 1/14 455/73 |
| 2014/0183106 A1 | 7/2014 | Kotsos et al. | |
| 2014/0230071 A1* | 8/2014 | Adam | G06F 21/60 726/26 |
| 2014/0267003 A1 | 9/2014 | Crnkovich et al. | |
| 2014/0276375 A1* | 9/2014 | Minkus | A61L 9/00 604/28 |
| 2014/0288947 A1* | 9/2014 | Simpson | G06F 19/3418 705/2 |
| 2015/0148623 A1* | 5/2015 | Benaron | A61B 5/4875 600/306 |
| 2015/0338926 A1* | 11/2015 | Park | G06F 3/014 345/156 |
| 2015/0341902 A1* | 11/2015 | Ryu | H04W 68/02 455/458 |
| 2016/0039424 A1* | 2/2016 | Hong | B60K 28/06 701/2 |
| 2016/0063232 A1* | 3/2016 | Seol | G04G 21/08 726/19 |
| 2016/0228633 A1* | 8/2016 | Welsch | A61M 5/142 |
| 2016/0266736 A1* | 9/2016 | Kirsch | G06F 3/0482 |
| 2016/0319826 A1* | 11/2016 | Shanks | H04L 67/125 |
| 2016/0342752 A1* | 11/2016 | Stueckemann | G06F 19/328 |
| 2017/0011210 A1* | 1/2017 | Cheong | G06F 21/32 |
| 2017/0065757 A1 | 3/2017 | Doyle et al. | |
| 2017/0079583 A1* | 3/2017 | Cardinali | A61B 5/14517 |
| 2017/0087290 A1 | 3/2017 | Medina et al. | |
| 2017/0103166 A1* | 4/2017 | Oh | A61B 5/02055 |
| 2017/0106151 A1 | 4/2017 | Schmidt et al. | |
| 2017/0136176 A1* | 5/2017 | Gray | A61M 5/142 |
| 2017/0348471 A1* | 12/2017 | Goto | A61M 1/30 |
| 2017/0351842 A1* | 12/2017 | Booth | G16H 40/63 |
| 2018/0018440 A1* | 1/2018 | Sugawara | A61M 5/142 |
| 2018/0120892 A1* | 5/2018 | von Badinski | G06F 3/14 |
| 2018/0132783 A1* | 5/2018 | Wang | A61B 5/681 |
| 2019/0313367 A1* | 10/2019 | Ryu | G06F 1/163 |
| 2020/0064781 A1* | 2/2020 | Shim | G04G 19/12 |
| 2020/0393900 A1* | 12/2020 | Park | G06F 3/011 |

FOREIGN PATENT DOCUMENTS

| | | | | |
|---|---|---|---|---|
| EP | 2939351 B1 * | 3/2017 | | G08B 21/20 |
| WO | 1999026686 | 6/1999 | | |
| WO | 2016059223 | 4/2016 | | |
| WO | 2017044327 | 3/2017 | | |
| WO | WO-2019187689 A1 * | 10/2019 | | A61M 5/145 |

OTHER PUBLICATIONS

International Search Report and Written Opinion in Application No. PCT/US2019/012263, dated Apr. 16, 2019, 18 pages.
U.S. Appl. No. 15/479,777, Weaver et al., filed Apr. 5, 2017.
"Patient Safety by Fresenius Medical Care; where new benchmarks are set," Cardioprotective Haemodialysis, Fresenius Medical Care Deutschland GmbH, 2012, 20 pages.
PCT International Preliminary Report on Patentability in International Appln. No. PCT/US2019/012263, dated Aug. 27, 2020, 13 pages.

* cited by examiner

WETNESS DETECTION WITH BIOMETRIC SENSOR DEVICE FOR USE IN BLOOD TREATMENT

TECHNICAL FIELD

The disclosure relates to systems, methods, and devices for patient identification and prescription retrieval, particularly during a dialysis treatment.

BACKGROUND

During dialysis treatment, arterial and venous access needles are typically inserted into a patient such that blood can be drawn from the patient through the arterial access needle, flown through a dialyzer to filter the blood, and then returned to the patient through the venous access needles. In some cases, the venous access needles may become dislodged. In the case that such an event goes unnoticed, an arterial access needle can continue to draw blood from the patient while the dislodged venous access needle does not return blood to the patient.

Additionally, prior to treatment the care technician must prepare the dialysis machine and the patient for dialysis treatment. Preparation involves disinfecting a wetness detector, setting up the dialysis machine with concentrates, priming the bloodlines, creating a blood connection with the patient, disinfect the ID card, insert the ID card, and confirming the treatment parameters. The described preparation also assumes that the ID card is not lost, damaged, or forgotten, otherwise the care technician must input the treatment parameters individually. The current dialysis preparation procedure is time consuming and prone to human error, resulting in a longer preparation time.

SUMMARY

This disclosure describes systems, methods and devices that can identify a patient using a biometric feature of the patient. Furthermore, the systems, methods and devices disclosed are configured to retrieve and upload a prescription of the identified patient for dialysis treatment.

In one aspect, a device that allows for patient identification comprises a housing, a biometric sensor coupled to the housing, the biometric sensor being configured to detect a biometric feature of a patient, and a signal transmitter configured to transmit data related to the detected biometric feature to a medical treatment machine for carrying out a medical treatment on the patient, wherein the patient identification device is configured to be secured to the patient during the dialysis treatment.

In another aspect, a method comprises reading biometric information using a biometric sensor of a device connected to a patient; processing biometric data, related to the biometric information using a control unit, in a manner such that the processed biometric data can be used to identify the patient, identifying the patient based on the processed data, and transmitting prescription data of the patient to a medical treatment machine to carry out a medical treatment on the patient.

In a further aspect, a method comprises reading biometric information using a biometric sensor of a device connected to a patient, processing biometric data related to the biometric information using a control unit, in a manner such that the processed biometric data can be used to identify the patient, identifying the patient based on the processed data, retrieving prescription data assigned to the patient identity from a cloud database, and transmitting prescription data of the patient to a medical treatment machine to carry out a medical treatment on the patient.

In another aspect, a medical treatment system comprises a medical treatment machine for carrying out a medical treatment on a patient, the medical treatment machine comprising a signal receiver and a processor or a control unit, and the treatment system further comprising a device that allows for patient identification, the device comprising a housing, a biometric sensor, coupled to the housing, the biometric sensor being configured to detect a biometric feature of a patient, and a signal transmitter configured to transmit data related to the detected biometric feature to a medical treatment machine for carrying out a medical treatment on the patient; wherein the patient identification device is configured to be secured to the patient during the dialysis treatment.

Embodiments may include one or more of the following features.

In some embodiments, the device may have a signal transmitter that is wireless signal transmitter. In certain embodiments, the device may further comprise a signal receiver for receiving signals from the medical treatment machine. In certain embodiments, the device has a biometric sensor that creates biometric data related to a detected biometric feature of the patient. In certain embodiments, the data transmitted by the signal transmitter is or derives from the biometric data. In some embodiments, the biometric feature of the patient is a fingerprint. In an alternative embodiment, the biometric feature is an iris. In certain embodiments, the biometric feature is a heat signature. In some embodiments, the device comprises a control unit configured to process the biometric data in a manner, such that the processed biometric data can be used to identify the patient. In certain embodiments, the device is configured to transmit the processed biometric data to a signal receiver of the medical treatment machine using the signal transmitter. In certain embodiments, the device is a medical device used in extracorporeal dialysis treatment. In certain embodiments, the device is reusable. In some embodiments, the reusable medical device is a wetness detector. In an alternative embodiment, the reusable medical device is a blood pressure cuff. In some embodiments, the sensor extends along the outer surface of a housing. In certain embodiments, the sensor is a finger print reader and is positioned so the patient can place a finger on the sensor during the treatment. In certain embodiments, the sensor is connected to the processor, control unit, and power source of the wetness sensor. In certain embodiments, the device is a bracelet.

In some embodiments, the method further comprises confirming the identity of the patient. In certain embodiments, confirming the patient's identity requires physical or verbal action by the operator of the medical treatment machine or the patient. In some embodiments, the device comprises a microphone. In certain embodiments, processing the biometric data and identifying the patient, are executed on the device, using a control unit of the device. In certain embodiments, identifying the patient includes, identifying the patient from the processed biometric data, retrieving the prescription data assigned to the patient from a memory of the device, and producing a transmittable signal containing at least the prescription data. In certain embodiments, processing the biometric data includes, transmitting the biometric data from the device to the medical treatment machine, and processing the biometric data using a control unit of the medical treatment machine. In some embodiments, identifying the patient includes, identifying the patient using the processed biometric data and transmitting the patient identity to a signal receiver of the device. In certain embodiments, transmitting the prescription data of the patient comprises, retrieving the prescription assigned to the patient from a memory of the device and transmitting a signal from the device to the medical treatment machine, containing at least the prescription data.

In some embodiments, the method further comprises confirming the identity of the patient. In certain embodiments, confirming the identity of the patient requires physical or verbal action by the operator of the medical treatment machine or the patient. In certain embodiments, the device comprises a microphone. In certain embodiments, processing the biometric data comprises transmitting biometric data from the device to the dialysis machine, processing the biometric data using a control device of the medical treatment machine. In certain embodiments, identifying the patient includes identifying the patient using the processed biometric data and transmitting the identity of the patient from the medical treatment machine to the cloud database. In certain embodiments, processing the biometric data comprises processing the biometric data using a control unit of the device. In certain embodiments, identifying the patient includes identifying the patient using a memory of the device, transmitting the identity of the patient from the device to the medical treatment machine, and transmitting the identity of the patient from the medical treatment machine to the cloud database.

In some embodiments, the device is in electronic communication with the medical treatment machine. In certain embodiments, the device identifies a patient using the biometric data and a memory of the device. In certain embodiments, the device further comprises a signal receiver and the medical treatment machine further comprises a signal transmitter. In certain embodiments, the system further comprises a data storage location in which patient data can be stored, retrieved, and transmitted. In certain embodiments, the data storage location is a memory of the device. In certain embodiments, the data storage location is a cloud database that is in wireless communication with the medical treatment machine. In certain embodiments, the medical treatment machine uses a single transmitter of the medical treatment machine to transmit a signal containing the identity of the patient to the cloud database. In certain embodiments, the medical treatment device uses a signal receiver of the medical treatment device to receive a signal from the cloud database containing prescription data of the patient. In certain embodiments, the device uses the signal transmitter to send a signal containing prescription data to the electronically coupled medical treatment machine.

These systems, methods, and devices may streamline part of the dialysis setup process, allowing clinicians and nurses to attend to additional patients. Furthermore, the systems, methods, and devices disclosed may reduce human error in treatment parameter input and allow for a detailed digital record of a patient's healthcare.

The details of one or more embodiments of the invention are set forth in the accompanying drawings and the description below. Other features, objects, and advantages of the invention will be apparent from the description and drawings, and from the claims.

DETAILED DESCRIPTION

Access to a circulatory system of the patient may require puncturing the skin of a patient using a needle, a catheter, or other devices to form an access. Procedures that can require access to the circulatory system can include dialysis, blood filtration, hemofiltration, blood donation, blood detoxification, apheresis, cardiac catheterizations, among other dialysis treatment procedures. During a dialysis treatment using a dialysis machine, the needle can place the circulatory system in fluid communication with an extracorporeal system. Blood circulates through the extracorporeal system and undergoes filtering within the extracorporeal system. Over the access site, a medical wetness sensor is placed. The medical wetness sensor is used to ensure that fluids within the extracorporeal system do not leak. The medical wetness sensor is designed to determine if a leak occurs at the access site. On the wetness sensor, a device for sensing and reading biometric information is used to identify the patient and upload a prescription of the patient to the dialysis machine, prior to treatment.

Figure 1:
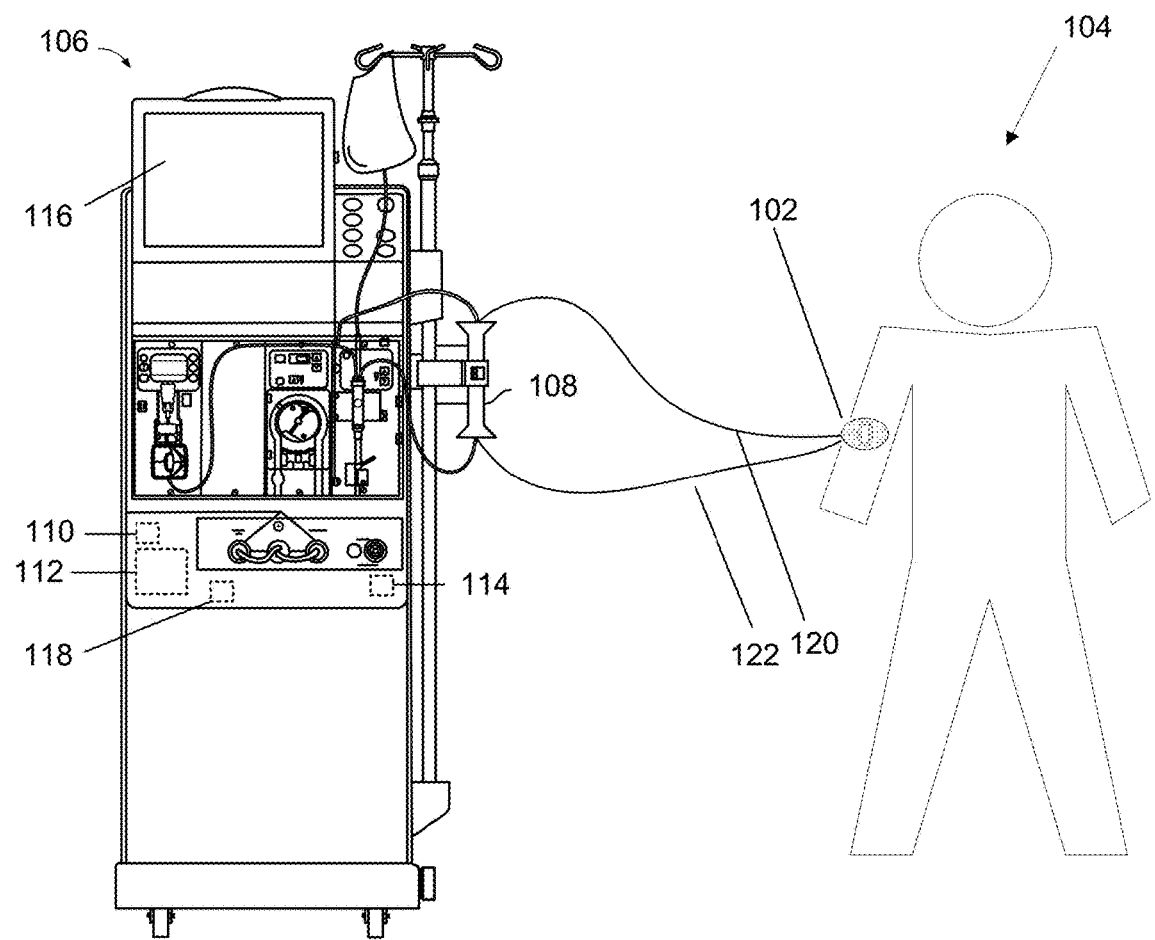
FIG. 1 shows a dialysis treatment system for dialysis treatment.

FIG. 1 shows a dialysis system 100 comprising a medical wetness device 102 removably attached to a patient 104, and a dialysis machine 106. The dialysis system 100 includes a dialysis machine 106 with a dialyzer 108 for performing a dialysis treatment on the patient 104. The patient 104 is connected to the dialysis machine 106 using an arterial bloodline 120 and a venous bloodline 122, in such a manner that the dialysis machine 106 and dialyzer 108 are a part of an extracorporeal blood circuit that removes and replaces blood via the bloodlines 120, 122. The dialysis machine 106 also comprises a power source 114 and a user interface 116.

The dialysis machine 106 further comprises a processor 110 and a signal receiver 112 for receiving signals from connected devices, such as the wetness device 102, and processing data sent in the received signal. The connected devices may be wirelessly connected to the dialysis machine 106. The processor 110 is configured to receive biometric information, process the biometric information such that it could be compared to known biometric data, and determine an identification match based on the comparison. The dialysis system may also comprise a signal transmitter 118 that is capable of transmitting processed or unprocessed data.

The medical wetness device 102 is attached to the patient 104 using gauze. The wetness device 102 may be placed over a venous needle or an arterial needle (not shown) and is capable of detecting medical wetness, such as blood. In some embodiments, an arterial needle inserted into an arterial access site of the patient 104 places the circulatory system of the patient 104 in fluid communication with the arterial line 120 and thus the extracorporeal blood circuit. Similarly, a venous needle (not shown) inserted into a venous access site places the circulatory system of the patient in fluid communication with the venous line 122 and thus the extracorporeal blood circuit. The arterial needle and the venous needle 112 typically inserted into a forearm of the patient 104, but other access sites can be used.

Figure 2:
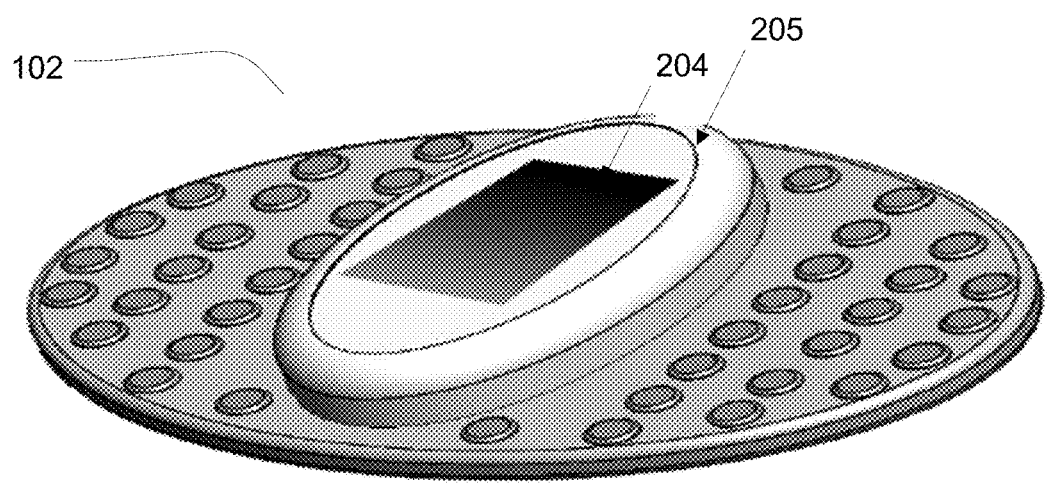
FIG. 2 shows an embodiment of a wetness sensor with an integrated biometric sensor.

FIG. 2 illustrates a wetness device 102 including biometric housing 205 and biometric sensor 204. The biometric sensor 204 is configured to scan or measure biometric information from the patient. The sensor 204 is located on the face of the wetness device 102, open to the environment during dialysis treatment. A section the housing 205, on which the sensor 204 is located, is slightly raised from the body of the wetness device 102. In some embodiments, the biometric sensor is a fingerprint scanner, and the biometric information is gathered by placing a finger of the patient onto the sensor. The housing is made of a resilient, biocompatible material and creates a protective housing for the electronic components of the sensor described in FIG. 3. The housing 205 supports the biometric sensor 204 and provides a flat surface suitable for accurate scanning or measuring.

Figure 3:
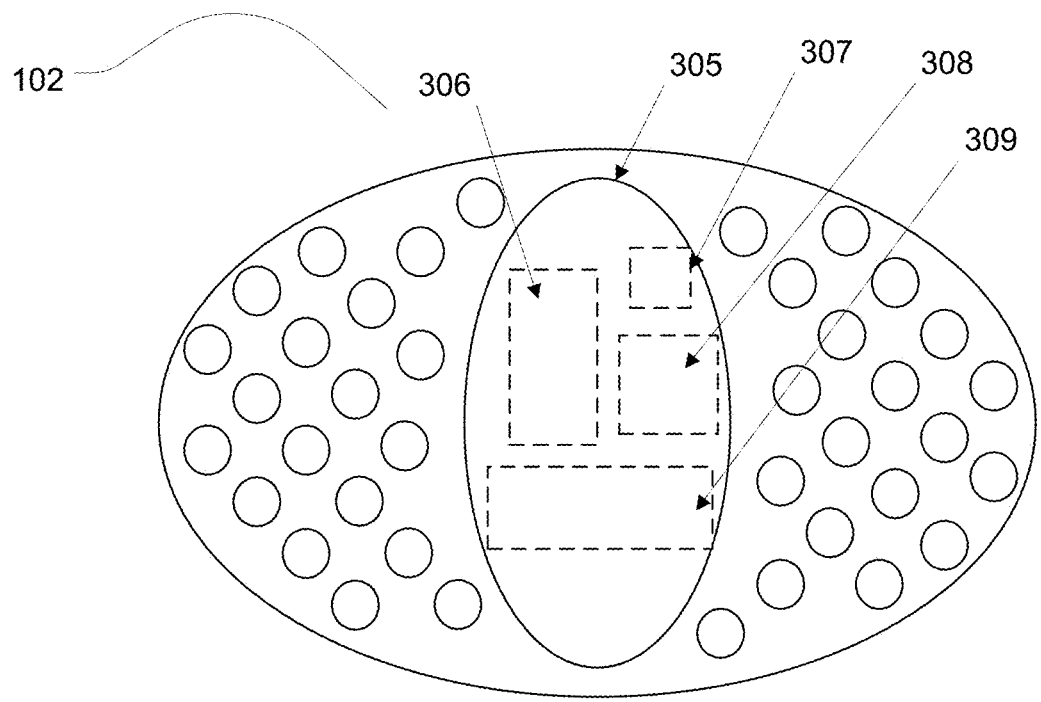
FIG. 3 shows a wetness sensor with an integrated biometric sensor.

FIG. 3 shows electronic components of an embodiment of the biometric sensor 204. FIG. 3 illustrates a housing 305, similar to the housing 205 in FIG. 2, and a signal transmitter 306. The device 102 may also include a signal receiver 307, a processor 308, a memory 309, or a combination thereof. The biometric sensor 204 shares electronic components with the medical wetness device 102, such as a power source, housing, or signal transmitter 306.

The wetness sensing device 102 shown in FIGS. 2 and 3 is flexible, thereby allowing the wetness sensing device 102 to conform to the skin and to the venous needle (not shown). In particular, an inner surface of the wetness sensing device 102 (e.g., a surface of the wetness sensing device 102 facing the venous access site) conforms to the skin. Because of the flexibility of the wetness sensing device 102, the geometry of the inner surface can closely match the geometry of the venous access site. Embodiments showing the flexible nature of the wetness sensor are shown in FIGS. 4 and 5.

Figure 4:
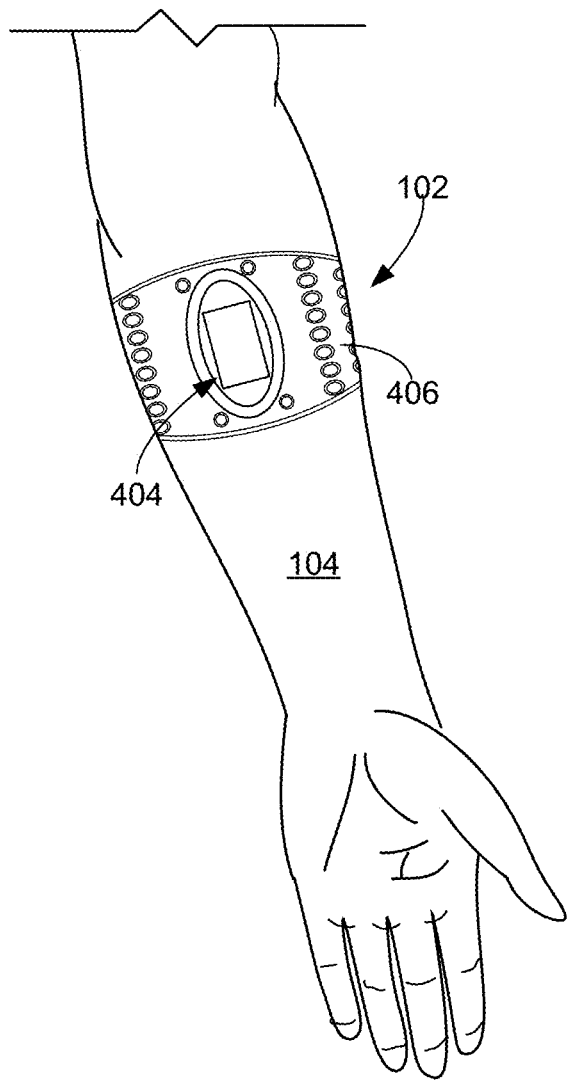
FIG. 4 shows a patient wearing a wetness sensor with an integrated biometric sensor.
Figure 5:
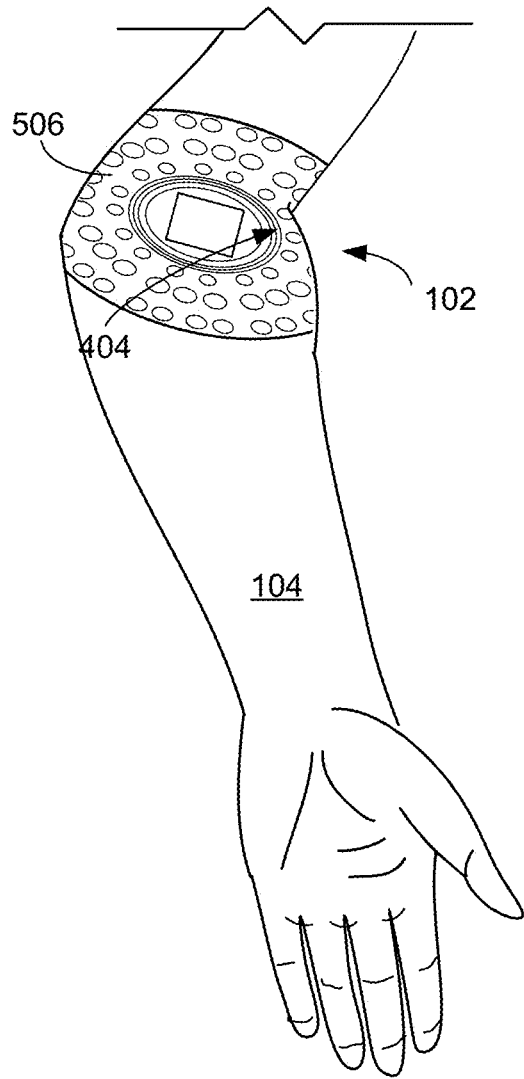
FIG. 5 shows an alternative embodiment of a patient wearing a wetness sensor with an integrated biometric sensor.

As shown in FIG. 4 in which the wetness sensing device 102 is placed on the patient 104 such that the base 406 of the wetness sensing device 102 bends along the contours of the patient 104. The biometric sensor 404 is located on a raised platform from base 406. Similarly, as shown in FIG. 5 in which the wetness sensing device is disposed on the patient such that the base 506 of the wetness sensing device 102 bends along the contours of the patient 104. The biometric sensor 404 is located on a raised platform from base 506. Hinge portions of the wetness sensing device bases 406, 506 enable the bending of the bases.

Figure 6A:
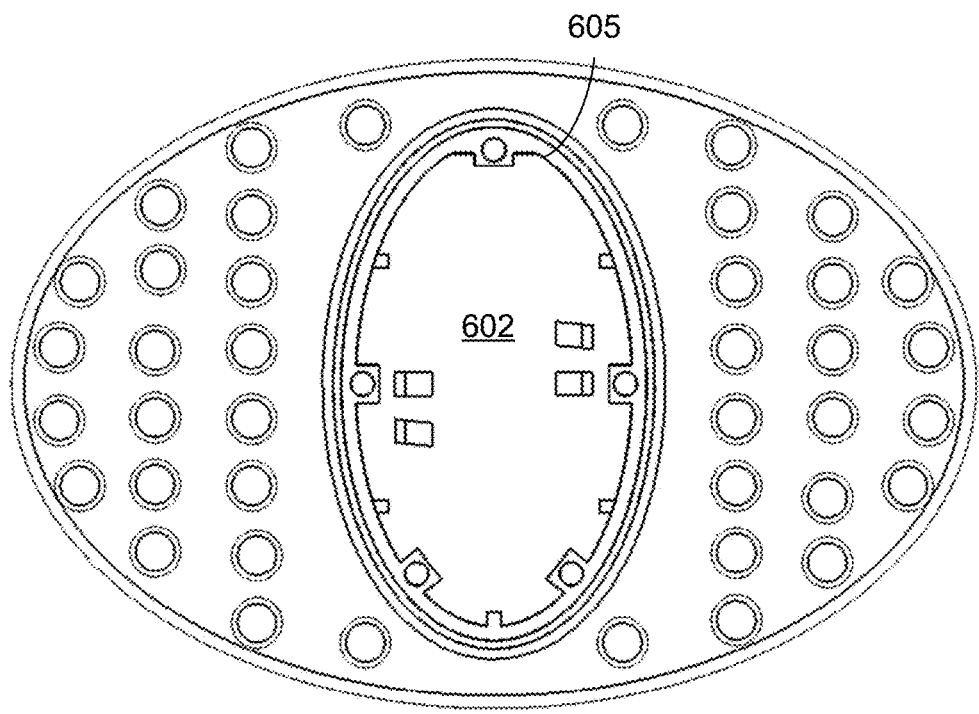
FIGS. 6A, 6B shows internal components of the wetness sensor with an integrated biometric sensor.

FIG. 6A shows internal components of wetness device 102 beneath the biometric sensor 204 (shown in FIG. 2). The view in FIG. 6A shows a separation plate 602 that separates the biometric sensor electronics shown in FIG. 3 from the electronics of the wetness device 102 show in FIG. 6B. In FIG. 6A, the separation plate 602 includes openings to provide access for wired electrical connections between the control circuitry of the biometric sensor 204 and the control circuitry of the wetness device 102. Often, electronic components are shared between the wetness device 102 and the biometric sensor 204 to minimize the number of parts, for example the biometric sensor 204 and the wetness device 102 may share an internal power source. Control circuitry of the wetness device 102 is contained within the housing 605. The control circuitry can include appropriate electrical components to control operations of the control circuitry.

Figure 6B:
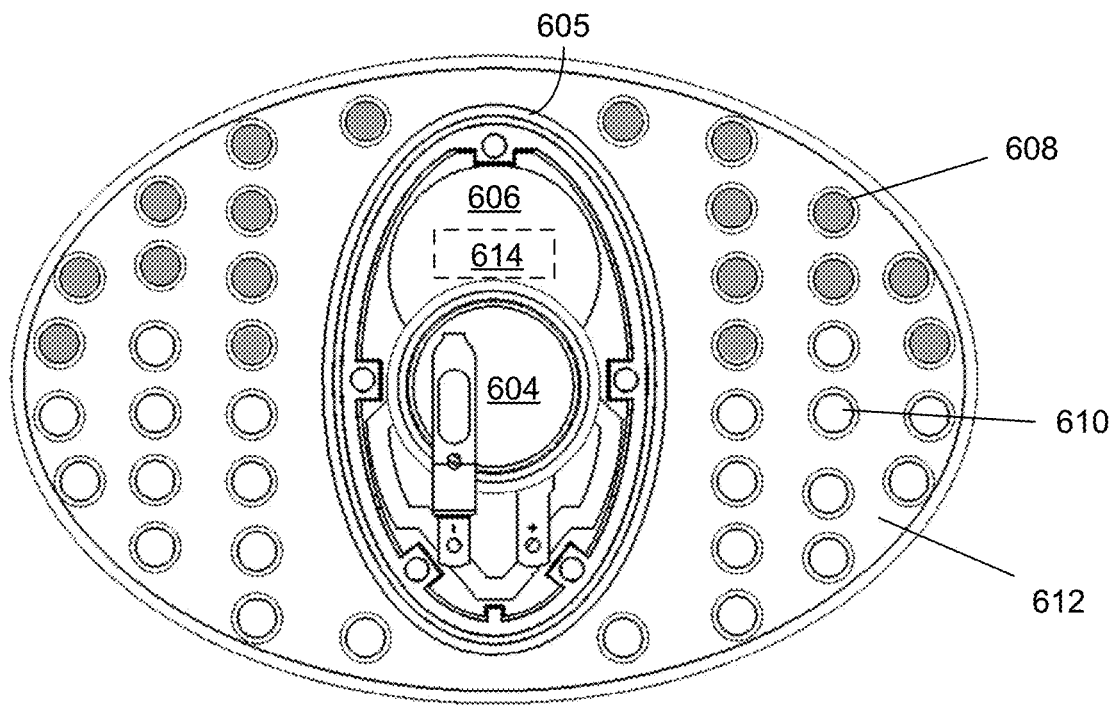

FIG. 6B illustrates control circuitry of the wetness device 102 housed within housing 605. The control circuitry includes an internal power source 604 and a microcontroller 606 to process, generate, transmit, and receive electrical signals. The control circuitry is electrically connected to a first electrical conductor 608 and a second electrical conductor 610 used for sensing medical wetness on the base of the wetness device 102.

The control circuitry can detect electrical continuity between the first and second electrical conductors 608, 610 by transmitting electrical test signals through the first and second electrical conductors 608, 610. For example, the control circuitry can transmit the test signals through one of the first and second electrical conductors 608, 610 and determine whether the test signals propagate through the other electrical conductor.

The control circuitry of the wetness device 102 is configured to detect a presence or an absence of a medical fluid electrically connecting the first and second electrical conductors 608, 610. In the absence of medical fluid, such as blood, the control circuitry can detect that the first and second electrical conductors 608, 610 do not form a closed electrical loop. In the presence of medical fluid, the control circuitry of the wetness device 102 can detect that the first and second electrical conductors 608, 610 form a closed electrical loop (e.g., are electrically continuous). In particular, the medical fluid can contact both the end portions of the first electrical conductor 608 and the end portions of the second electrical conductor 610 to form the closed electrical loop. In the presence of the medical fluid, the electrical test signal transmitted through the first and second electrical conductors 608, 610 indicate electrical continuity between the first electrical conductor 608 and the second electrical conductor 610.

The control circuitry of the wetness device 102 can determine that an electrical resistance below a predetermined threshold indicates that the first and second electrical conductors 608, 610 form the closed electrical loop or are electrically continuous. Electrical resistances below a threshold between, for example, 500 Kohms and 1 Mohm can indicate electrical continuity between the first and second electrical conductors that could occur in the presence of medical fluid.

In response to detecting electrical continuity through the first and second electrical conductors 608, 610, the control circuitry of the wetness device 102 can generate an electrical signal indicating the presence of medical fluid along the inner surface of the base 612. Similarly, in response to detecting electrical isolation between the first and second electrical conductors 608, 610 (e.g., the first and second electrical conductors 608, 610 are not electrically connected), the control circuitry can generate an electrical signal indicating the absence of medical fluid along the inner surface 612. In some cases, in response to detecting the electrical isolation, the control circuitry can simply not transmit an electrical signal. The first and second electrical conductors 608, 610 are thus configured to cause the control circuitry of the wetness device 102 to generate a signal indicating the absence or presence of medical fluid on the inner surface.

The control circuitry can include a wireless transceiver 614, which can, based on the electrical signal, generate a wireless signal indicating the absence of medical fluid or the presence of medical fluid. The wireless signal can be transmitted to a wireless transceiver of an extracorporeal system, a dialysis machine, or other treatment device (e.g., the wireless receiver 112 of FIG. 1). The wireless transceiver 616 can transmit the wireless signal until the wireless transceiver 616 receives a wireless stop signal including instructions to stop transmitting the wireless signal. For example, the treatment device can transmit a wireless stop signal to the wireless transceiver 616 after the medical fluid leak causing the presence of the medical fluid has been resolved.

The control circuitry receives power from a power source 604 to execute various electrical operations. The control circuitry can use the power to transmit the test signals to detect an absence or presence of electrical continuity that can be caused by the absence or presence of medical fluid on the inner surface of the base 612. The control circuitry of the biometric sensor 204 may also receive power from power source 604. In some implementations, the power source 604 is removably housed in the housing 605. An upper housing portion may be removable from the lower housing portion so that the power source 604 can be removed and inserted. As a result, the power source 604 can be replaceable in an event that the power source 604 does not have sufficient power to energize the control circuitry of the wetness device 102 and the biometric sensor 204.

While in the absence of medical fluid, the wetness sensing device 102 can operate in an idle state in which the control circuitry transmits the electrical test signals without generating the electrical signal and the wireless signal. The idle state has a reduced power requirement, as the control circuitry does not operate the wireless transceiver 614 during the idle state.

Figure 7C:
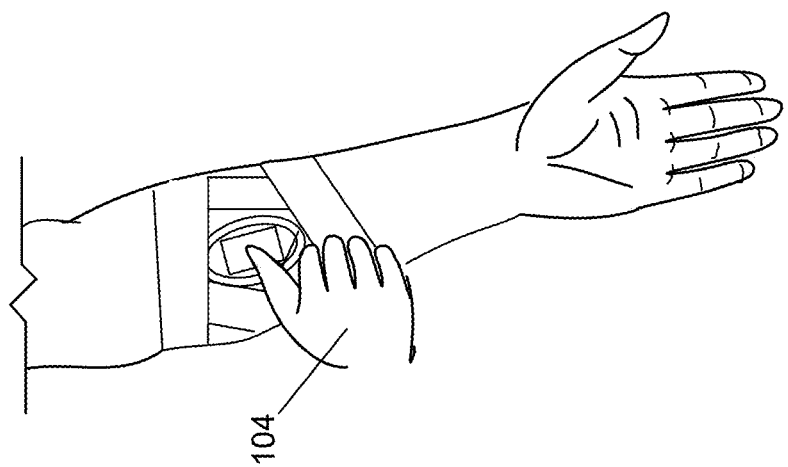
FIGS. 7A-C shows a wetness device with a biometric sensor placed on the skin of a patient and used for identification.
Figure 7B:
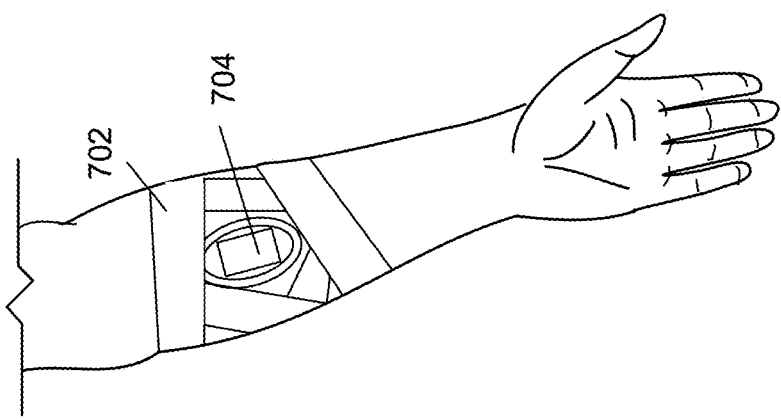
Figure 7A:
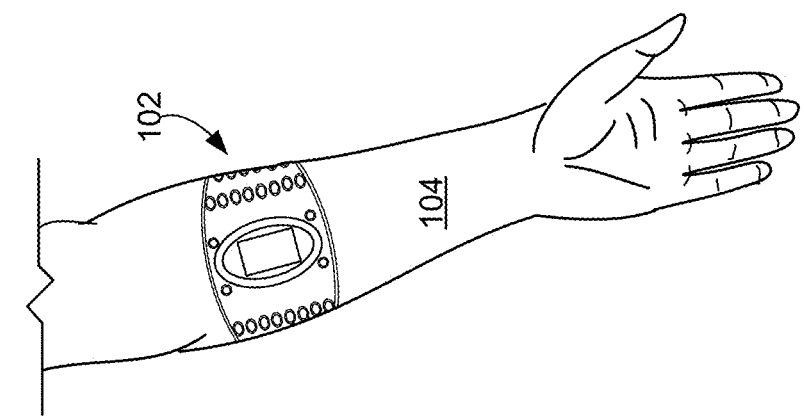

FIGS. 7A-7C show a procedure for applying and using the wetness sensing device 102 coupled with a biometric device 204. During use, the wetness sensing device 102 is disposed on the patient with gauze 105 positioned between the wetness sensing device 102 and the skin of the patient 104. The wetness sensing device 102 is positioned over the venous needle, and a cloth or gauze 702 is wrapped around the wetness sensing device 102 to the fix wetness sensing device 102 in place. FIG. 7A shows the patient 104 with the wetness device 102 on the forearm of the patient 104. The forearm is a common placement for the arterial and venous bloodline attachment sites, however another location on the body of the patient 104 is acceptable. The base of the wetness device 102 is flexible and is wrapped around the forearm on top of the bloodline attachment site. FIG. 7B shows the device wrapped in cloth or gauze 702 in order to fix the device 102 to the forearm. The gauze 702 covers the base of the device 102 but does not cover the biometric sensor 704, allowing the patient 104 access to the biometric sensor. Alternatively, the device can be secured onto a patient using a cuff with an opening in the shape of the biometric sensor. The cuff is placed on the arm of the patient so that the biometric sensor extends through the opening, allowing the patient access to the biometric sensor. The cuff diameter can be adjustable and secured using Velcro. In some embodiments, the gauze is wrapped around the forearm, creating a first layer. The wetness device 102 is then placed on top of the first layer of gauze and is secured to the patient using a second layer of gauze. FIG. 7C illustrates a patient using an opposite hand to place a finger onto the biometric sensor 704. The biometric sensor 704, in this case a finger print reader, scans the fingerprint and the patient 104 is identified. The identification method is described in more detail in FIGS. 8 and 9.

After patient identification, the wetness sensing device 102 is primarily used to sense medical wetness. In response to detecting leakage of blood, the wetness device 102 can transmit wireless signals to alert external systems of the leak. The wetness sensing device 102 includes a wireless transceiver 306 (shown in FIG. 3) that can communicate with a wireless receiver 112 (shown on FIG. 1) of the dialysis machine 106. Upon detection of a leak, the dialysis machine 106 can alert the patient or a care technician to resolve the leak, stop the treatment, or otherwise change the course of treatment in response to the leak. The wetness sensing device 102 can be flexible and therefore conformable to the skin of the patient so that the wetness sensing device can be disposed on contours of the patient's body while maintaining close contact with the skin. Blood leakages from the access site can accordingly be quickly and reliably detected.

Figure 8:
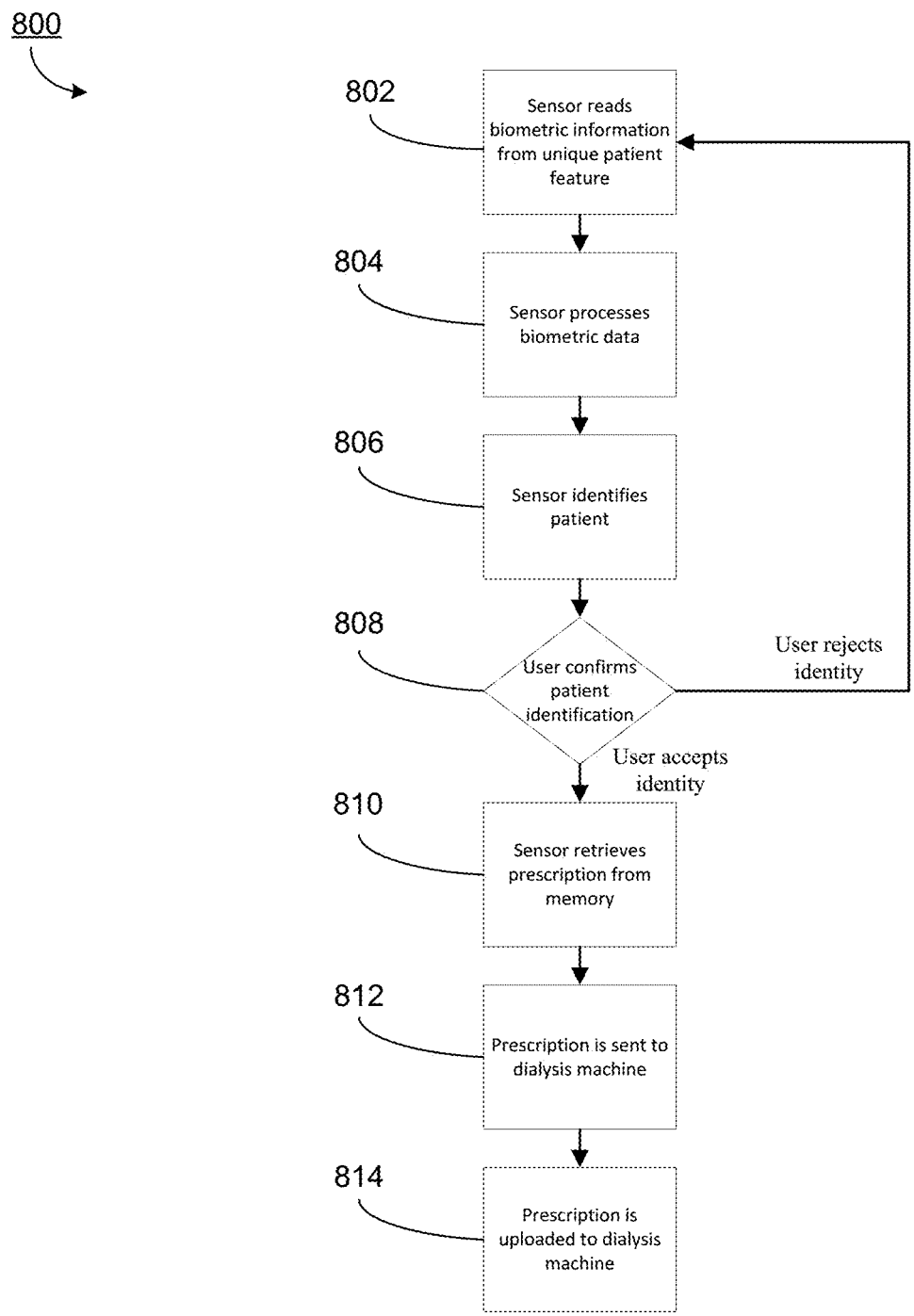
FIG. 8 shows a procedure for identifying and uploading a prescription using a dialysis treatment system.
Figure 9:
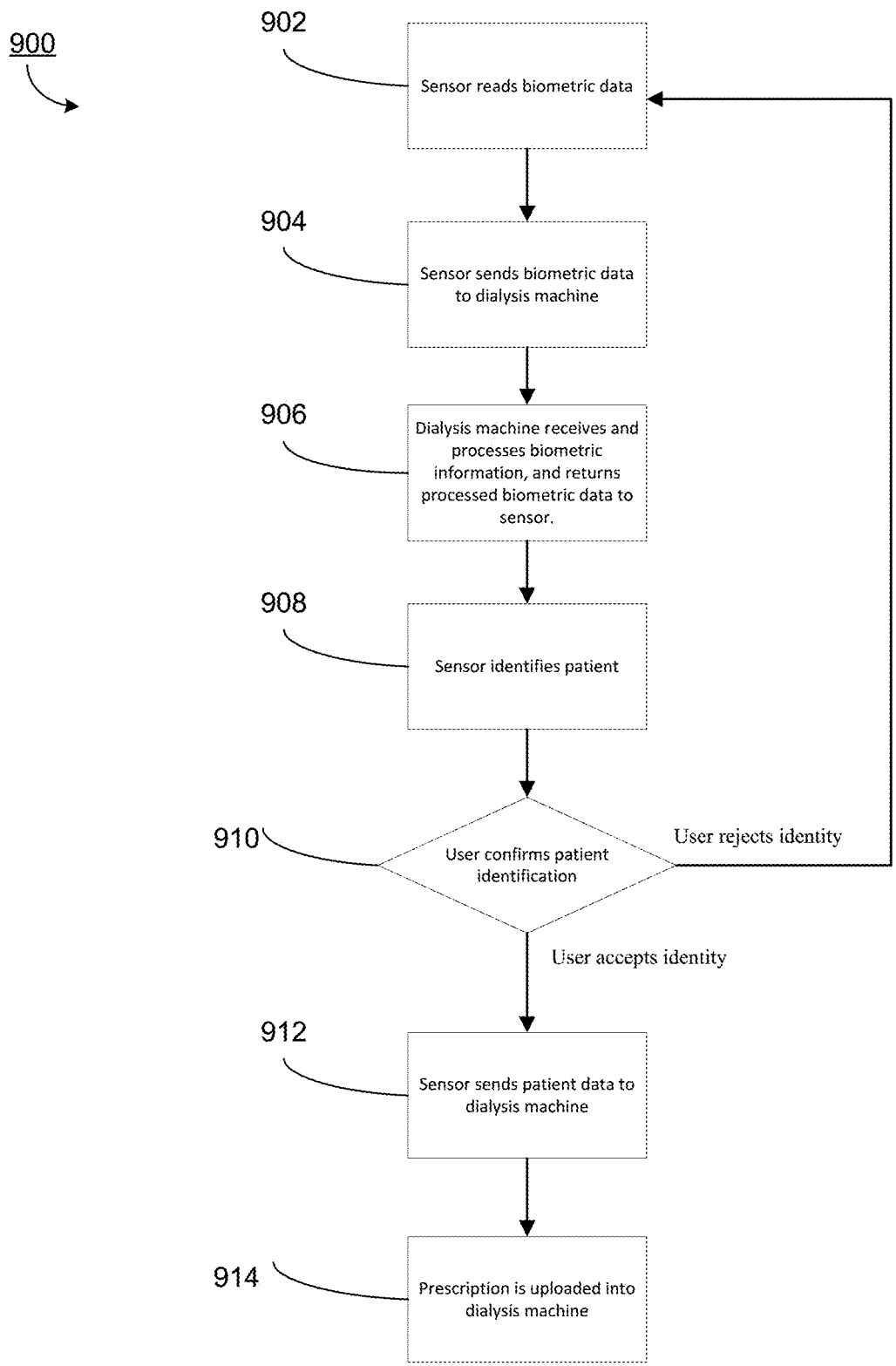
FIG. 9 shows a procedure for identifying and uploading a prescription using a dialysis treatment system.

FIG. 8 and FIG. 9 illustrate procedures for two embodiments of the device. The embodiment described in FIG. 8 is a procedure 800 for a dialysis system, with a biometric sensor coupled to a medical wetness sensing device and a dialysis machine. The coupled sensor includes a power source, a housing, a signal transmitter, processor, a memory, and a confirmation mechanism. The confirmation mechanism may be located on or within the coupled device and requires the patient to confirm a determined identity using a physical or verbal action. In an embodiment for which the patient gives verbal confirmation, the coupled device includes a microphone. The memory of the biometric sensor stores prescription data of the patient. The dialysis machine comprises a signal receiver and a processor.

The patient and dialysis machine are prepared for dialysis treatment by connecting the venous and arterial bloodlines to the patient and to the dialysis machine. A first layer of gauze is wrapped around the needle and the wetness sensor is placed above the first layer of gauze. The coupled sensor is secured by wrapping additional gauze around the housing of the wetness sensor, but leaving at least the biometric sensor exposed. The patient scans the desires biometric feature onto the biometric sensor 802, producing biometric information related to the biometric feature. The biometric information is processed into biometric data. The biometric information gathered by the biometric sensor, is changed into biometric data using a processor and is compared to a known packet of biometric data assigned to a patient identity. If the measured biometric data is significantly similar to the control biometric data, the patient identity is confirmed 806 within the biometric sensor and a user confirmation is prompted 808. If the user confirmation is rejected, the device returns to step 802 and prepares to measure a biometric feature. Otherwise, the user confirms the patient identity and the coupled device retrieves the patient prescription assigned to the patient identity from the memory of the biometric sensor 810. The memory may also include additional patient data for example, previous treatment data, additional biometric data, medication allergies, or other information useful for dialysis treatment. The coupled device then sends the patient prescription to a wirelessly connected dialysis machine 812 configured to upload the prescription based on the transmitted prescription data 814.

In FIG. 8, the coupled sensor processes the biometric information into biometric data, however, FIG. 9 illustrates a procedure 900 in which the dialysis machine processes the biometric information. The patient and dialysis machine are prepared in the same manner. The coupled biometric sensor and wetness device may comprise a power source, a signal transmitter, a signal receiver, and a memory. The memory contains at least the prescription data of the patient identity. The dialysis machine comprises a processor, a signal receiver, and a signal transmitter.

The venous and arterial bloodlines are connected to the patient and to the dialysis machine. A first layer of gauze is wrapped around the needle and the wetness sensor is placed above the first layer of gauze. The coupled sensor is secured by wrapping additional gauze around the housing of the wetness sensor, but leaving at least the biometric sensor exposed. The patient scans the desires biometric feature onto the biometric sensor, producing biometric information related to the biometric feature 902. The biometric information is transmitted from the coupled sensor using the signal transmitter and is received by the dialysis machine using the signal receiver of the dialysis machine. The biometric information is processed into biometric data using the processor of the dialysis machine and is transmitted back to the coupled sensor using a signal transmitter of the dialysis treatment device 904. The coupled sensor receives the biometric data using the signal receiver of the coupled sensor and compares the biometric data with a known packet of biometric data assigned to a patient identity. If the measured biometric data is significantly similar to the known packet of biometric data, the patient identity is confirmed within the sensor 908 and a user confirmation is prompted 910. If the user rejects the identity, the sensor returns to step 902 and prepares to read a biometric feature of a patient. If the used confirms the identity, the coupled sensor retrieves the patient prescription assigned to the patient identity from the memory of the biometric sensor and sends the patient prescription to a wirelessly connected dialysis machine 912. The memory of the biometric sensor may also store additional patient data for example, previous treatment data, additional biometric data, medication allergies, or other information useful for dialysis treatment. The dialysis machine is configured to upload the prescription 914 based on the transmitted prescription data.

Figure 10:
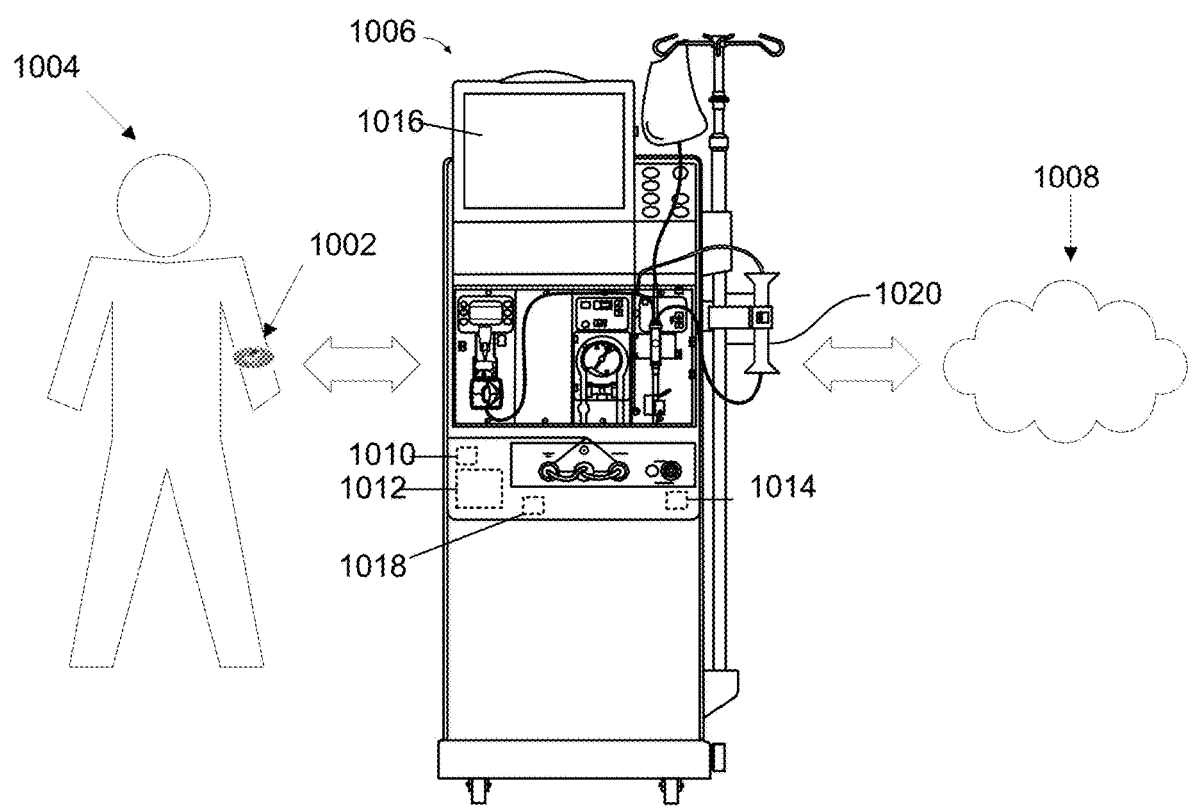
FIG. 10 shows a dialysis treatment system with a user, a wetness sensor, a dialysis machine, and an electronic cloud.

FIG. 10 shows an alternative embodiment of the dialysis system 1000. The dialysis system 1000 includes a patient 1004 connected to a dialysis machine 1006. The dialysis system 1000 further comprises a wetness detector with a biometric sensor 1002 and an electronic cloud 1008 used for storing patient information and prescription data. The electronic cloud 1008 and dialysis machine 1006 are in electronic communication. The dialysis machine 1006 is comparable to the dialysis machine of FIG. 1 in that the dialysis machine 1006 also comprises a processor 1010, for processing data sent in the signal, a dialyzer 1020, and a signal receiver 1012, for receiving signals from connected devices, such as the wetness sensor 1002.

The electronic cloud 1008 is configured to store patient data, including the prescription for a dialysis treatment. The patient data can be retrieved from the cloud 1008 and transmitted to a connected device, such as the dialysis machine 1006. In some embodiments, the cloud 1008 is capable of identifying a patient using biometric data and retrieving the prescription of the identified patient.

The wetness sensor with a biometric sensor 1002 is wirelessly connected to the dialysis machine 1006. The processor 1010 of the dialysis machine 1006, may be configured to receive raw biometric information and process the biometric information such that it could be compared to known biometric data. Alternatively, the processor 1010 of the dialysis machine 1006 may be configured to receive and transmit processed data or identification data, acting as a pathway from the sensor 1002 and the electronic cloud 1008. The dialysis machine 1006 may also comprise a signal transmitter 1018 that is capable of transmitting unprocessed data, processed data, or identification data to the cloud 1008. Similarly, the electronic cloud 1008 is configured to receive unprocessed biometric information, processed biometric data, or identification data. Regardless of the received signal, the electronic cloud 1008 sends the prescription data for an identification match to the dialysis machine 1006, unless no identity match was found. In the case that the electronic cloud 1008 receives unprocessed biometric information, the electronic cloud 1008 will process the biometric information into biometric data, compare the newly processed biometric data to known biometric data, identify the patient, retrieve the prescription data of the identified patient, and return the prescription data and the identified patient data to the dialysis machine 1006. In the case that the electronic cloud receives processed biometric data the electronic cloud 1008 will compare the processed biometric data to known biometric data, identify the patient, retrieve the prescription data of the identified patient, and return the prescription data and the identified patient data to the dialysis machine 1006. In the case that the electronic cloud 1008 receives information data, the electronic cloud 1008 will retrieve the prescription data of the identified patient in the identification data, and return the prescription data to the dialysis machine 1006.

Figure 11:
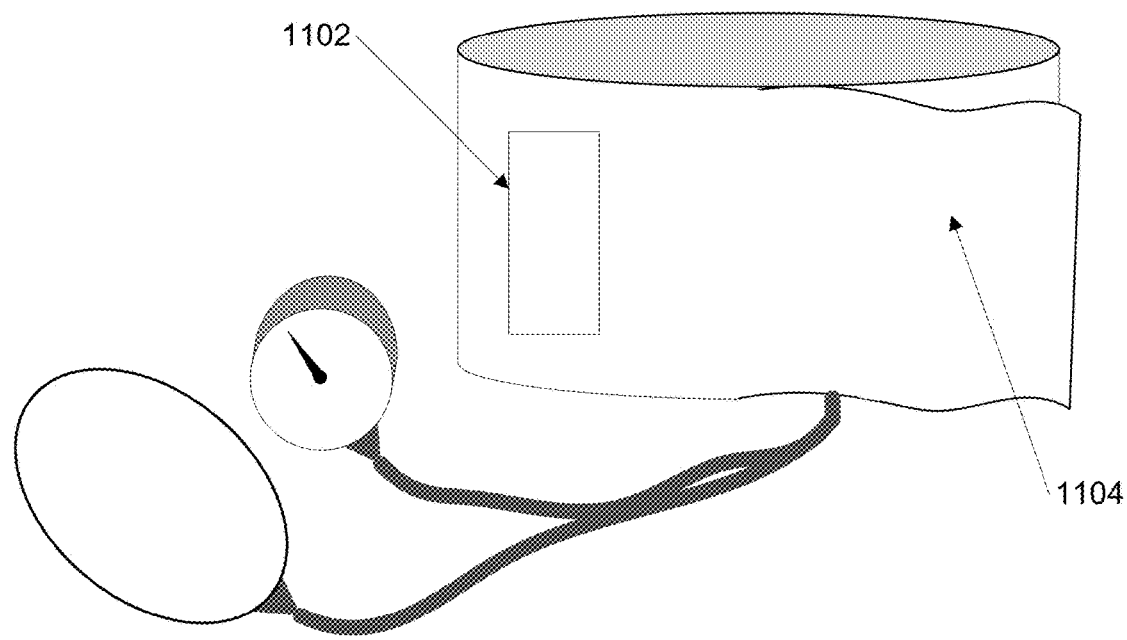
FIG. 11 shows and alternative embodiment of the dialysis treatment system.
Figure 12:
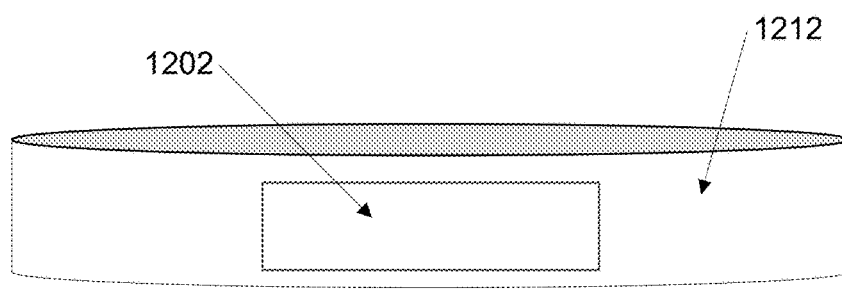
FIG. 12 shows an alternative embodiment of the dialysis treatment system.

In some embodiments the biometric sensor may be coupled to a reusable device. FIGS. 11 and 12 illustrate alternative embodiments for the biometric sensor. The biometric sensor can be coupled with any reusable device used in dialysis treatment. FIG. 11 illustrates a biometric sensor 1102 coupled to a blood pressure cuff 1104. The coupled device is in communication with a dialysis machine. The biometric sensor 1102 comprises a memory, a signal receiver, a signal transmitter, a processor, a microphone, and/or a power source. If the blood pressure cuff is connected to the dialysis machine, the biometric sensor may connect to the dialysis machine in the same manner. For example, if the blood pressure cuff is connected to the dialysis machine using a connection wire, the biometric sensor may also use the connection wire to communicate with the dialysis machine. Alternatively, if the blood pressure cuff is connected wirelessly, the biometric sensor 1102 may communicate with the dialysis machine wirelessly. The biometric sensor 1102 acts similarly to wetness device embodiment, in that the biometric sensor 1102 is configured to read a biometric feature and send unprocessed data, processed data, or identification data to a dialysis machine. An additional similarity is that that biometric sensor may share electronic components with the blood pressure cuff to reduce the number of moving parts.

FIG. 12 illustrates an alternative embodiment in which the biometric sensor 1202 is coupled to a bracelet 1212. The bracelet may be used specifically for identification purposes, and comprises a memory, a signal receiver, a signal transmitter, a processor, a microphone, and a power source. In an exemplary embodiment, the biometric sensor is located on an outward facing housing of the bracelet, however the sensor may also be facing inwards if the biometric feature is easily measured with an inward facing sensor. The biometric sensor 1202 acts similarly to wetness device 102 in that the biometric sensor 1202 is configured to read a biometric feature and send unprocessed data, processed data, or identification data to a dialysis machine. The bracelet is wirelessly connected to a dialysis machine.

The biometric sensor embodied in the described figures is finger print scanner, designed to measure a fingerprint as the biometric feature. The biometric sensor may also be configured to sense other biometric features, including but not limited to a heat signature or an iris. A heat signature is an infrared signal emitted by all humans due to their emitted heat, specifically from blood vessels. Capillaries create a pattern beneath a person's skin, unique to individuals. The pattern of the heat emitted by the capillaries or larger blood vessels can be used as a unique biometric identifier. The biometric sensor may also be configured to sense proximate RFID chips, using the signal receiver. For example, the RFID chips could be housed in a clinician ID card, a patient ID card, or a blood pressure cuff.

Figure 13:
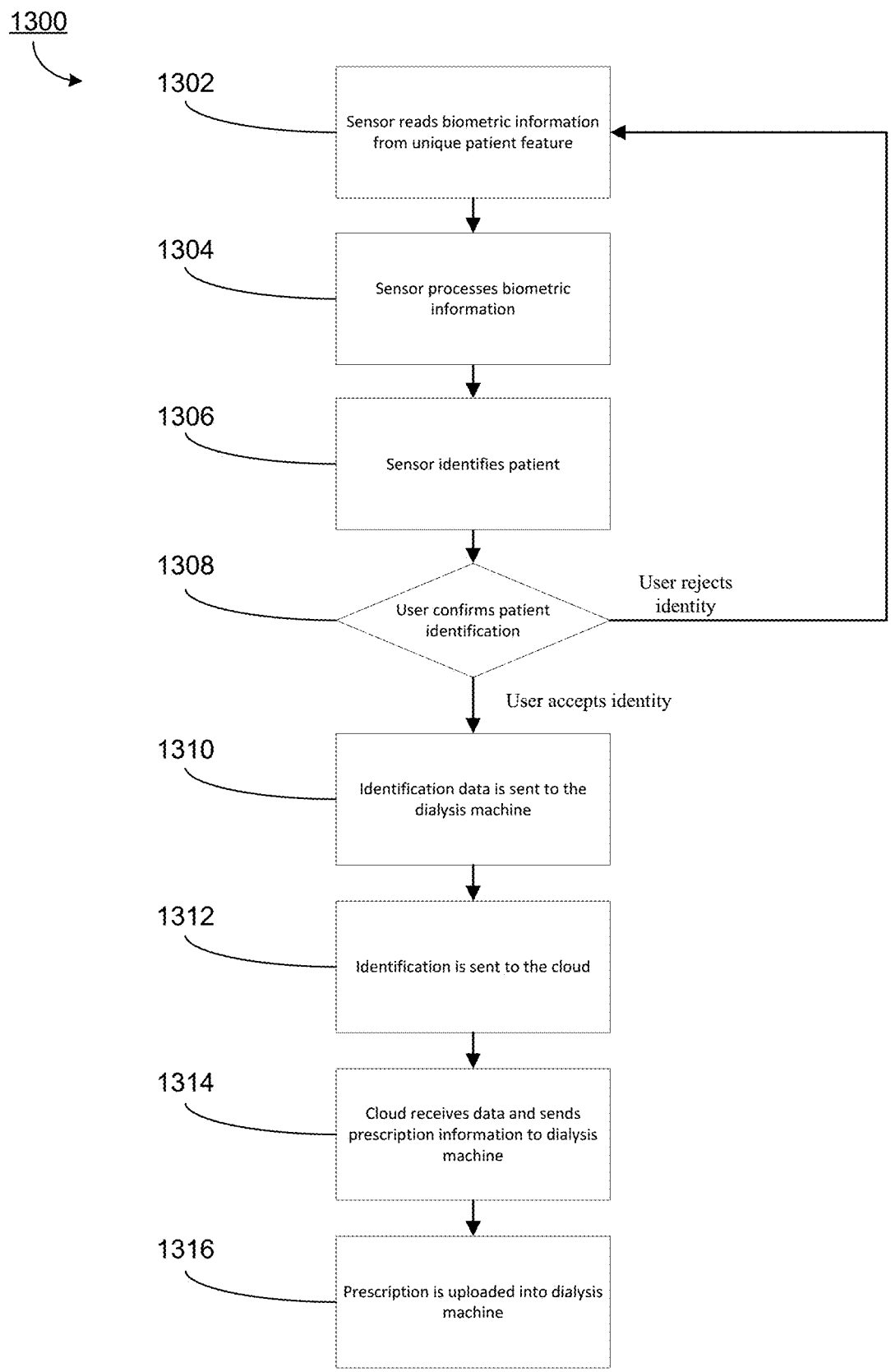
FIG. 13 shows a procedure for identifying and uploading a prescription using a dialysis treatment system.
Figure 14:
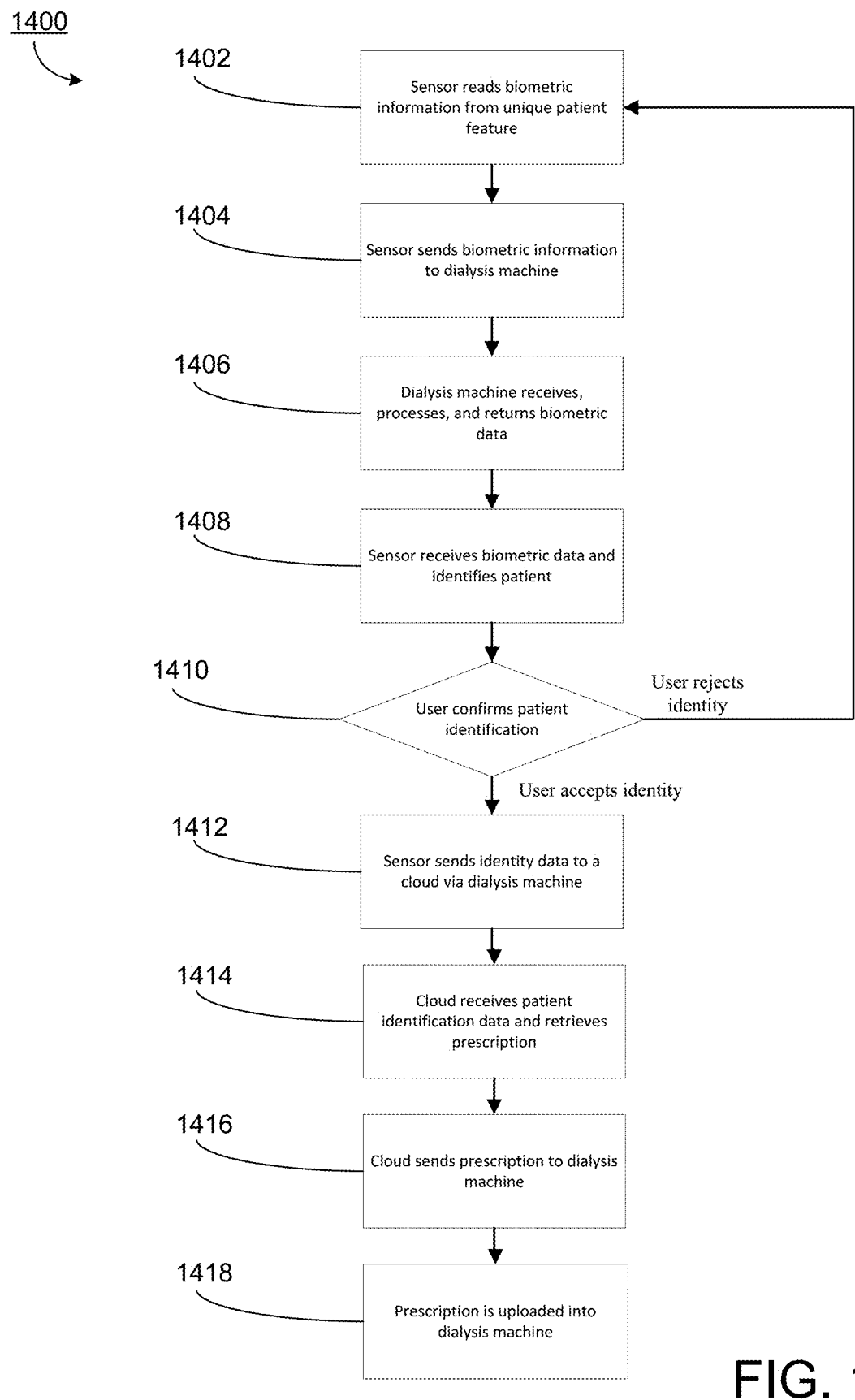
FIG. 14 shows a procedure for identifying and uploading a prescription using a dialysis treatment system.

FIG. 13 and FIG. 14 show procedures for identifying a patient and uploading a prescription for a dialysis system with a biometric sensor coupled to a medical wetness detector, a dialysis machine, and a cloud database. The cloud database stores prescription data of a patient or multiple patients. The patient and dialysis machine are prepared in the same manner as in the description of FIG. 8.

FIG. 13 shows a procedure 1300 that includes a dialysis system with a wetness device coupled to a biometric sensor and a dialysis machine in communication with the coupled sensor. The dialysis further comprises an electronic cloud in wireless communication with the dialysis machine. The coupled biometric sensor and wetness device contains a power source, a signal transmitter, processor, a memory, and a confirmation mechanism. The memory stores a patient identity data and prescription data that can be accessed by comparing a known biometric feature to a measured biometric feature. The confirmation mechanism may be located on or within the coupled device and requires the patient to confirm a determined identity using a physical or verbal action. In an embodiment for which the patient gives verbal confirmation, the coupled device includes a microphone. The dialysis machine comprises a signal transceiver, and a signal transmitter. The cloud database and dialysis machine are in wireless communication.

The patient and dialysis machines are prepared for dialysis treatment, such that the venous and arterial bloodlines are connected to the patient and to the dialysis machine. A first layer of gauze is wrapped around the needle and the wetness sensor is placed above the first layer of gauze. The coupled sensor is secured by wrapping additional gauze around the housing of the wetness sensor, but leaving at least the biometric sensor exposed. The patient scans the desires biometric feature onto the biometric sensor, producing biometric information related to the biometric feature 1302. The biometric information can be processed into biometric data. The biometric information gathered by the biometric sensor is changed into biometric data using a processor and is compared to a known packet of biometric data assigned to a patient identity 1304. If the measured biometric data is significantly similar to the control biometric data, the patient identity is confirmed within the sensor 1306 and a user confirmation is prompted 1308. The user confirms the identity and identity information is sent to the dialysis machine 1310. Alternatively, the patient identity can be confirmed within the coupled device and transmitted to the dialysis treatment device for confirmation. The confirmed identity data is transmitted to the cloud database 1312. The cloud database receives the confirmed patient identification data and retrieves the patient prescription data 1314. The cloud database may also store additional patient data for example, previous treatment data, additional biometric data, or other information useful for dialysis treatment. The cloud database transmits at least the prescription data to the dialysis machine and the dialysis machine is able to upload the prescription based 1316 on the transmitted prescription data.

FIG. 14 discloses an embodiment that uses a system comprising a biometric sensor coupled to a medical wetness detector, a dialysis machine, and a cloud database, wherein the couple database comprises prescription data of a patient or multiple patients. The coupled device may comprise a signal transmitter and a memory. The memory contains a patient identification linked to a biometric data of a known biometric feature. The dialysis machine may comprise a signal transmitter, a signal receiver, and a processor. The cloud database stores prescription data of patients linked to known identification data, and may also include additional patient data for example, previous treatment data, additional biometric data, or other information useful for dialysis treatment.

The patient and dialysis machines are prepared for dialysis treatment, such that the venous and arterial bloodlines are connected to the patient and to the dialysis machine. A first layer of gauze is wrapped around the needle and the wetness sensor is placed above the first layer of gauze. The coupled sensor is secured by wrapping additional gauze around the housing of the wetness sensor, but leaving at least the biometric sensor exposed. The patient scans the desires biometric feature onto the biometric sensor, producing biometric information related to the biometric feature 1402. The biometric information is transmitted from the coupled device using the signal transmitter and is received by the dialysis machine using the signal receiver of the dialysis machine 1404. The biometric information is processed into biometric data using the processor of the dialysis treatment and returns the biometric data to the sensor. The sensor receives the biometric data and compares the biometric data with a known packet of biometric data assigned to the patient identification. If the measured biometric data is significantly similar to the control biometric data, the patient identity is confirmed within the sensor 1408 and a user confirmation is prompted 1410. The confirmed identity data is transmitted to the dialysis machine and the dialysis machine transmits the confirmed identity data to the cloud database 1412. The cloud database receives the confirmed patient identification data and retrieves the patient prescription data 1414. The cloud database may also store additional patient data for example, previous treatment data, additional biometric data, or other information useful for dialysis treatment. The cloud database transmits at least the prescription data to the dialysis machine 1416. The dialysis machine is able to upload the prescription based on the transmitted prescription data 1418.

A number of embodiments of the invention have been described. Nevertheless, it will be understood that various modifications may be made without departing from the spirit and scope of the invention. The exemplary embodiments in FIGS. 1-14 are illustrative of the device but are not limiting. A combination of the procedures or a combination of part of the procedures described in the figures are considered within the scope of the disclosure. For example, in some embodiments the dialysis machine may contain a memory in which patient data is stored, as opposed to the sensor. In an alternative embodiment, the biometric information may be processed in the cloud rather than in the dialysis machine or the sensor. In certain embodiments, the dialysis machine may facilitate a user confirmation using a user interface. In an alternative embodiment in which the biometric sensor comprises a microphone, the microphone may be used by the clinician and/or patient to record notes during treatment that can be saved with the patient data.

What is claimed is:

1. A method comprising:
reading biometric information using a biometric sensor of a wetness detection device, wherein the entire wetness detection device is disposed on a patient and is configured to detect a fluid leak at a venous or arterial access site on the patient, wherein the wetness detection device includes an inner surface that is disposed over the venous or arterial access site on the patient and that flexibly conforms to the skin of the patient,
processing biometric data, related to the biometric information using a control unit, in a manner such that the processed biometric data can be used to identify the patient,
identifying the patient based on the processed biometric data,
retrieving prescription data assigned to the patient from a memory internal to the wetness detection device, transmitting the prescription data of the patient to a dialysis machine; and
causing the dialysis machine to perform a medical treatment on the patient based on the prescription data.

2. The method of claim 1 further comprising confirming the identity of the patient.

3. The method of claim 2, wherein confirming the patient's identity comprises physical or verbal action by an operator of the dialysis machine or the patient.

4. The method of claim 2, wherein the wetness detection device comprises a microphone.

5. The method of claim 1, wherein the control unit is part of the wetness detection device such that the processing the biometric data and identifying the patient are executed on the wetness detection device.

6. The method of claim 1, wherein the identifying the patient includes producing a transmittable signal containing at least the prescription data.

7. The method of claim 1, wherein the control unit is part of the dialysis machine, and the method includes transmitting the biometric data from the wetness detection device to the dialysis machine.

8. The method of claim 7, wherein the identifying the patient includes transmitting the patient identity to a signal receiver of the wetness detection device.

9. The method of claim 8, wherein the transmitting the prescription data of the patient comprises transmitting a signal from the wetness detection device to the dialysis machine, the signal containing at least the prescription data.

10. A method comprising:
reading biometric information using a biometric sensor of a wetness detection device disposed on a patient, wherein the wetness detection device is configured to detect a fluid leak at a venous or arterial access site on the patient, wherein the wetness detection device includes an inner surface that is disposed over the venous or arterial access site on the patient and that flexibly conforms to the skin of the patient,
processing biometric data, related to the biometric information using a control unit, in a manner such that the processed biometric data can be used to identify the patient,
identifying the patient based on the processed biometric data,
prompting, on a dialysis machine, a confirmation of the patient identity,
retrieving prescription data assigned to the patient identity from a cloud database,
transmitting the prescription data assigned to the patient to the dialysis machine, and
causing the dialysis machine to perform a medical treatment on the patient based on the prescription data.

11. The method of claim 10 further comprising confirming the identity of the patient.

12. The method of claim 11, wherein the confirming the identity of the patient comprises physical or verbal action by an operator of the medical treatment machine or the patient.

13. The method of claim 10, wherein the wetness detection device comprises a microphone.

14. The method of claim 10, wherein the control unit is part of the dialysis machine, and the method comprises transmitting the biometric data from the wetness detection device to the dialysis machine.

15. The method of claim 14, wherein the identifying the patient includes identifying the patient using the processed biometric data and transmitting the identity of the patient from the dialysis machine to the cloud database.

16. The method of claim 10, wherein the control unit is part of the wetness detection device.

17. The method of claim 16, wherein the identifying the patient includes identifying the patient using a memory of the wetness detection device, transmitting the identity of the patient from the wetness detection device to the dialysis machine, and transmitting the identity of the patient from the dialysis machine to the cloud database.

18. The method of claim 10, wherein the entire wetness detection device is disposed on the patient.

* * * * *